(12) United States Patent
Wang et al.

(10) Patent No.: US 9,232,352 B2
(45) Date of Patent: Jan. 5, 2016

(54) BACKHAUL LINK ASSISTED INDOOR SPECTRUM USE ENFORCEMENT SOLUTION FOR MBAN SERVICES

(75) Inventors: Dong Wang, Ossining, NY (US); Monisha Ghosh, Chappaqua, NY (US); Delroy Smith, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 87 days.

(21) Appl. No.: 14/001,683

(22) PCT Filed: Feb. 24, 2012

(86) PCT No.: PCT/IB2012/050853
§ 371 (c)(1),
(2), (4) Date: Aug. 27, 2013

(87) PCT Pub. No.: WO2012/117320
PCT Pub. Date: Sep. 7, 2012

(65) Prior Publication Data
US 2013/0337842 A1  Dec. 19, 2013

Related U.S. Application Data

(60) Provisional application No. 61/447,829, filed on Mar. 1, 2011.

(51) Int. Cl.
*H04W 4/02* (2009.01)
*H04W 16/20* (2009.01)
(Continued)

(52) U.S. Cl.
CPC .............. *H04W 4/021* (2013.01); *A61B 5/002* (2013.01); *A61B 5/0022* (2013.01);
(Continued)

(58) Field of Classification Search
None
See application file for complete search history.

(56) References Cited

U.S. PATENT DOCUMENTS

| 7,737,850 | B2 | 6/2010 | Malik |
| 7,769,396 | B2 | 8/2010 | Alizadeh-Shabdiz et al. |

(Continued)

FOREIGN PATENT DOCUMENTS

| WO | 2004109992 A1 | 12/2004 |
| WO | 2008103915 A1 | 8/2008 |

OTHER PUBLICATIONS

Smith, D.; Comments of Philips Healthcare Systems; Amendment of the Commission's Rules to Provide Spectrum for the Operation of Medical Body Area Networks; 2009; pp. 1-67. http://fjallfoss.fcc.gov/ecfs/document/view?id=7020040931.

(Continued)

*Primary Examiner* — Charles Appiah
*Assistant Examiner* — Margaret G Mastrodonato

(57) ABSTRACT

A medical system includes one or more MBAN devices which acquire and communicate patient data. One or more medical body area network (MBAN) systems include the one or more MBAN devices communicating the patient data with a hub device via short-range wireless communication. The communication of the patient data via the short-range wireless communication being within a predefined spectrum. The hub device receives patient data communicated from the one or more MBAN devices, communicates with a central monitoring station via a longer range communication and one or more access points (AP), and determines the location of the MBAN system in reference to a healthcare facility. The one or more MBAN devices are inhibited from transmitting within the predefined spectrum when the MBAN hub device is located outside the healthcare facility.

4 Claims, 4 Drawing Sheets

Figure 1:
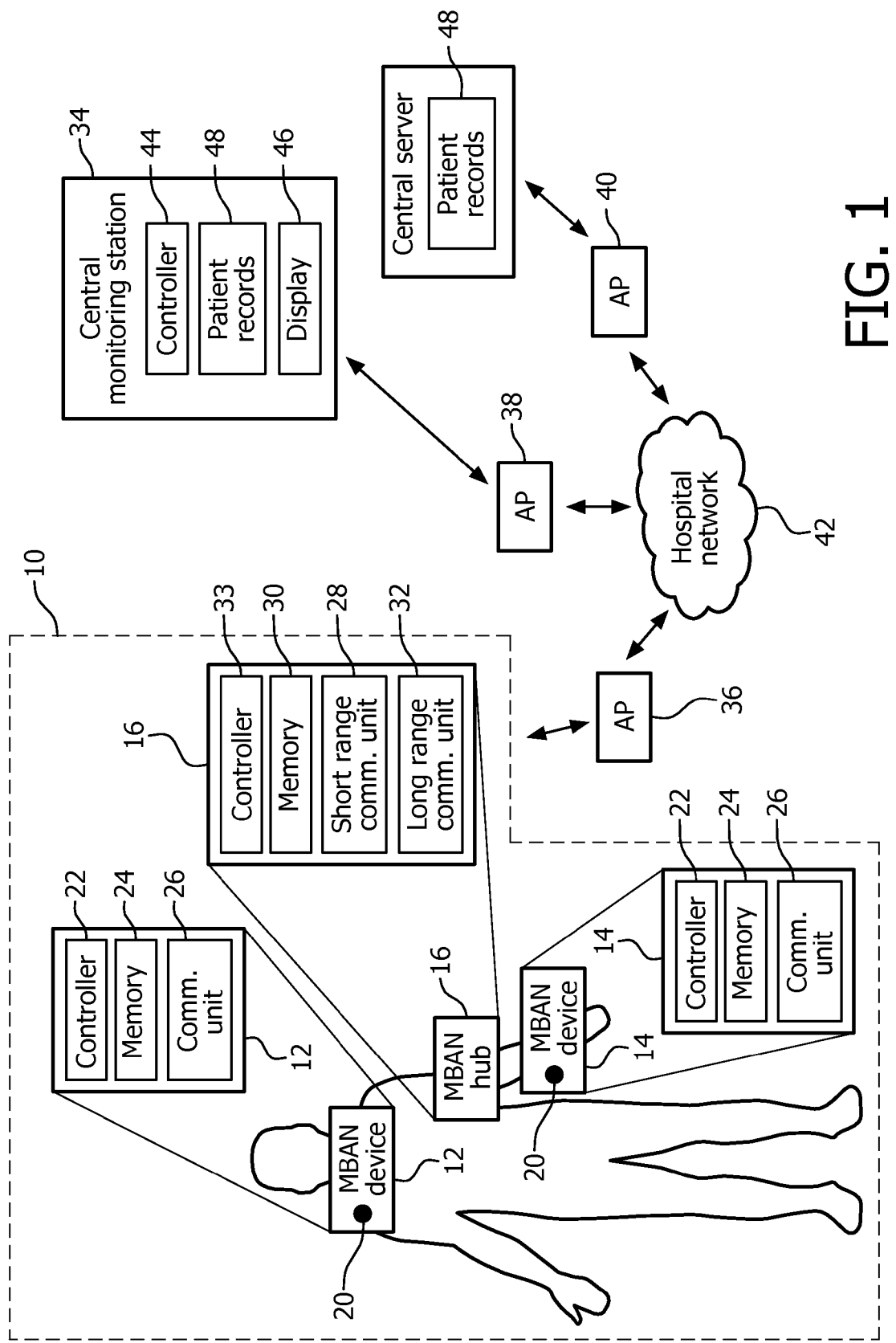

(51) Int. Cl.
*H04W 48/04* (2009.01)
*H04W 84/18* (2009.01)
*A61B 5/00* (2006.01)
*G06F 19/00* (2011.01)
*A61B 5/024* (2006.01)
*A61B 5/0402* (2006.01)
*A61B 5/08* (2006.01)

(52) U.S. Cl.
CPC ......... *A61B 5/0024* (2013.01); *G06F 19/3406* (2013.01); *G06F 19/3418* (2013.01); *H04W 48/04* (2013.01); *A61B 5/024* (2013.01); *A61B 5/0402* (2013.01); *A61B 5/0816* (2013.01); *H04W 16/20* (2013.01); *H04W 84/18* (2013.01)

(56) References Cited

U.S. PATENT DOCUMENTS

| | | |
|---|---|---|
| 2002/0029258 A1 | 3/2002 | Mousseau et al. |
| 2005/0181779 A1* | 8/2005 | Jones et al. .................. 455/421 |
| 2006/0143292 A1* | 6/2006 | Taubenheim et al. ......... 709/225 |
| 2006/0148482 A1 | 7/2006 | Mangold |
| 2006/0202834 A1 | 9/2006 | Moriwaki |
| 2008/0077026 A1 | 3/2008 | Banet et al. |
| 2008/0228045 A1* | 9/2008 | Gao et al. ...................... 600/301 |
| 2010/0246544 A1 | 9/2010 | Brisebois et al. |

OTHER PUBLICATIONS

Wang, J., et al.; Emerging cognitive radio applications: A Survey; 2011; IEEE Communications Magazine; pp. 74-81.

* cited by examiner

BACKHAUL LINK ASSISTED INDOOR SPECTRUM USE ENFORCEMENT SOLUTION FOR MBAN SERVICES

CROSS REFERENCE TO RELATED APPLICATIONS

This application is a national filing of PCT application Serial No. PCT/IB2012/050853, filed Feb. 24, 2012, published as WO 2012/117320 A1 on Sep. 7, 2012, which claims the benefit of U.S. provisional application Ser. No. 61/447,829 filed Mar. 1, 2011, which is incorporated herein by reference.

The present application relates to medical monitoring and clinical data devices for monitoring the physiological condition of a patient. It finds particular application in the restriction and enforcement of an MBAN spectrum for MBAN services and applications.

The rapid growth in physiological sensors, low power integrated circuits and wireless communication has enabled a new generation of medical body area networks (MBAN) to be used to monitor patients. MBANs provide low-cost wireless patient monitoring (PM) without the inconvenience and safety hazards posed by wired connections, which can trip medical personnel or can become detached so as to lose medical data. In the MBAN approach, multiple low cost sensors are attached at different locations on or around a patient, and these sensors take readings of patient physiological information such as patient temperature, pulse, blood glucose level, electrocardiographic (ECG) data, or so forth. The sensors are coordinated by at least one proximate hub or gateway device to form the MBAN. The hub or gateway device communicates with the sensors using embedded short-range wireless communication radios for example conforming with an IEEE 802.15.4 (Zigbee) short-range wireless communication protocol. Information collected by the sensors is transmitted to the hub or gateway device through the short-range wireless communication of the MBAN, thus eliminating the need for cables. The hub or gateway device communicates the collected patient data to a central patient monitoring (PM) station via a wired or wireless longer-range link for centralized processing, display and storage. The longer-range network may, for example, include wired Ethernet and/or a wireless protocol such as Wi-Fi or some proprietary wireless network protocol. The PM station may, for example, include an electronic patient record database, display devices located at a nurse's station or elsewhere in the medical facility, or so forth.

MBAN monitoring acquires patient physiological parameters. Depending upon the type of parameter and the state of the patient, the acquired data may range from important (for example, in the case of monitoring of a healthy patient undergoing a fitness regimen) to life-critical (for example, in the case of a critically ill patient in an intensive care unit). Because of this there is a strict reliability requirement on the MBAN wireless links due to the medical content of the data. However, the current spectrum allocations and regulations for medical wireless connectivity do not meet the strict requirements of MBAN, including medical-grade link robustness, ultra low-power consumption and low-cost, due to either limited bandwidth or uncontrolled interference.

Short-range wireless communication networks, such as MBAN systems, tend to be susceptible to interference. The spatially distributed nature and typically ad hoc formation of short-range networks can lead to substantial spatial overlap of different short range networks. The number of short-range communication channels allocated for short range communication systems is also typically restricted by government regulation, network type, or other factors. The combination of overlapping short-range networks and limited spectral space (or number of channels) can result in collisions between transmissions of different short range networks. These networks can also be susceptible to radio frequency interference from other sources, including sources that are not similar to short-range network systems.

It is known to employ frequency spectrum regulation policies to increase the spectrum use efficiency. One trend is to allocate an MBAN spectrum specifically for MBAN applications and services as secondary users of the spectrum that has been previously allocated to other services on a primary basis. For example, it has been proposed in the U.S. to open the 2360-2400 MHz band (MBAN spectrum), currently assigned to others, to MBAN services as a secondary user. Similar proposals have been made or are expected to be made in other countries. The wide bandwidth, interference-free and good propagation properties of the MBAN spectrum would meet the strict requirements for medical-grade connectivity.

In order to achieve co-existence between primary users and secondary users, some restrictions (or spectrum regulation rulings) would be put on the spectrum use of secondary users. To protect the primary users, restrictions would need to be placed on the use of the MBAN spectrum. For example, the MBAN spectrum could only be used by MBAN devices while they are located within healthcare facilities. If an MBAN device is outside the healthcare facility, the MBAN device could only transmit outside the MBAN spectrum. This means that an MBAN device can transmit within the MBAN spectrum only within the healthcare facility and the MBAN devices must switch to a new channel outside the MBAN spectrum to communicate when the MBAN devices are outside the healthcare facility. To accomplish this, enforcement mechanisms are needed and would be integrated in the future MBAN systems to guarantee the compliance with the MBAN regulations.

The simplest in-facility spectrum use enforcement would be manual administration. For example, when an MBAN system is prescribed by a health care professional to monitor a patient in a healthcare facility, a nurse or other healthcare staff will manually enable the hub device to use the MBAN spectrum. When a patient is going to move outside the healthcare facility, for example, due to discharge from hospital, a healthcare staff will manually disable and prohibit the hub device from operating in the MBAN spectrum. The manually enable/disable operations could be implemented by manually entering a passcode on the hub device or connect the hub device with a specific device (for example, plug a USB key on the hub device) and a program running on the hub device or the specific device could automatically enable/disable the MBAN spectrum access of the hub device.

However, such manual administration method need a large amount of staff intervention and significantly reduces workflow efficiency in hospital. Also it is difficult to guarantee the compliance of the in-facility use ruling. For example, the healthcare staff may forget to enable/disable the hub device, which would result in either the inefficiency use of the MBAN spectrum (assume the hub device by default will use other spectrum when activated) or violation of the in-facility use ruling (MBAN devices will still use the MBAN spectrum when going outside without be disabled). Further, patients with on-body MBAN devices operating in the MBAN spectrum may wander and leave the facility from time to time. The wandering of patients could be out of control of healthcare staff and break the in-facility use rulings.

The present application provides a new and improved system and method for access point assisted MBAN spectrum use enforcement for MBAN services which overcomes the above-referenced problems and others.

In accordance with one aspect, a medical system is provided. The medical system includes one or more MBAN devices which acquire and communicate patient data. One or more medical body area network (MBAN) systems include the one or more MBAN devices communicating the patient data with a hub device via short-range wireless communication. The communication of the patient data via the short-range wireless communication being within a predefined spectrum. The hub device receives patient data communicated from the one or more MBAN devices, communicates with a central monitoring station via a longer range communication and one or more access points (AP), and determines the location of the MBAN system in reference to a healthcare facility. The one or more MBAN devices are inhibited from transmitting within the predefined spectrum when the MBAN hub device is located outside the healthcare facility.

In accordance with another aspect, a method is provided. The method includes collecting patient data by one or more medical body area network (MBAN) devices, determining a location of an MBAN system, communicating the collected patient data from the one or more MBAN devices through the MBAN system to a hub device via short-range wireless communication, wherein the communication via short-range wireless communication within a predefined spectrum is permitted only within a healthcare facility; and communicating the collected patient data from the hub device to a central monitoring station via longer range wireless communication through the one or more APs and determines the location of the MBAN system from the one or more APs.

One advantage resides in the enforcement of the MBAN spectrum with MBAN systems.

Another advantage resides in the use of access point information to determine whether an MBAN system is within or outside a healthcare facility to control use of the MBAN spectrum.

Another advantage resides in improved healthcare workflow efficiency, safety, and clinical outcome.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically illustrates a medical body area network (MBAN) system in accordance with the present application.

Figure 2:
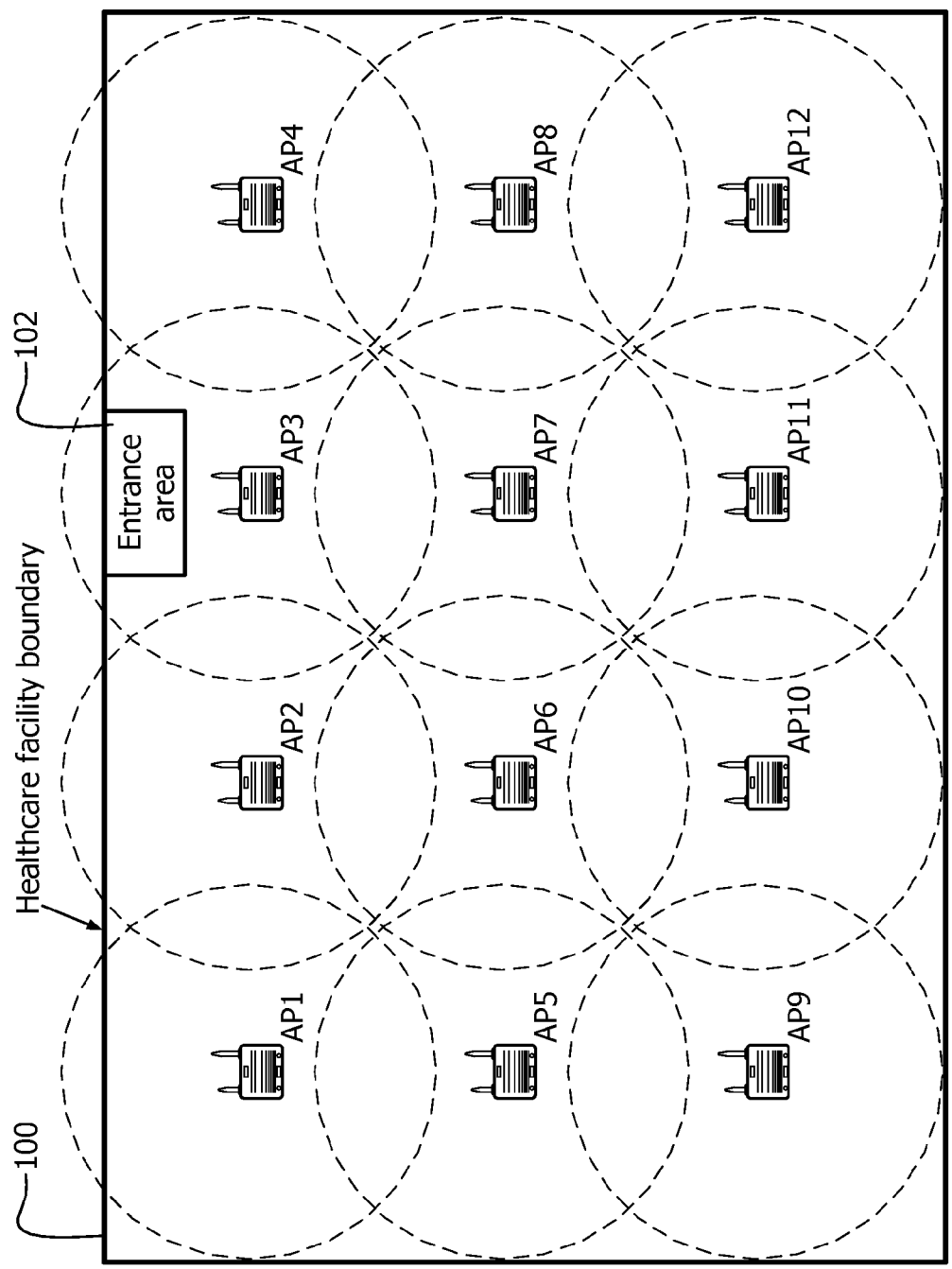
Figure 3:
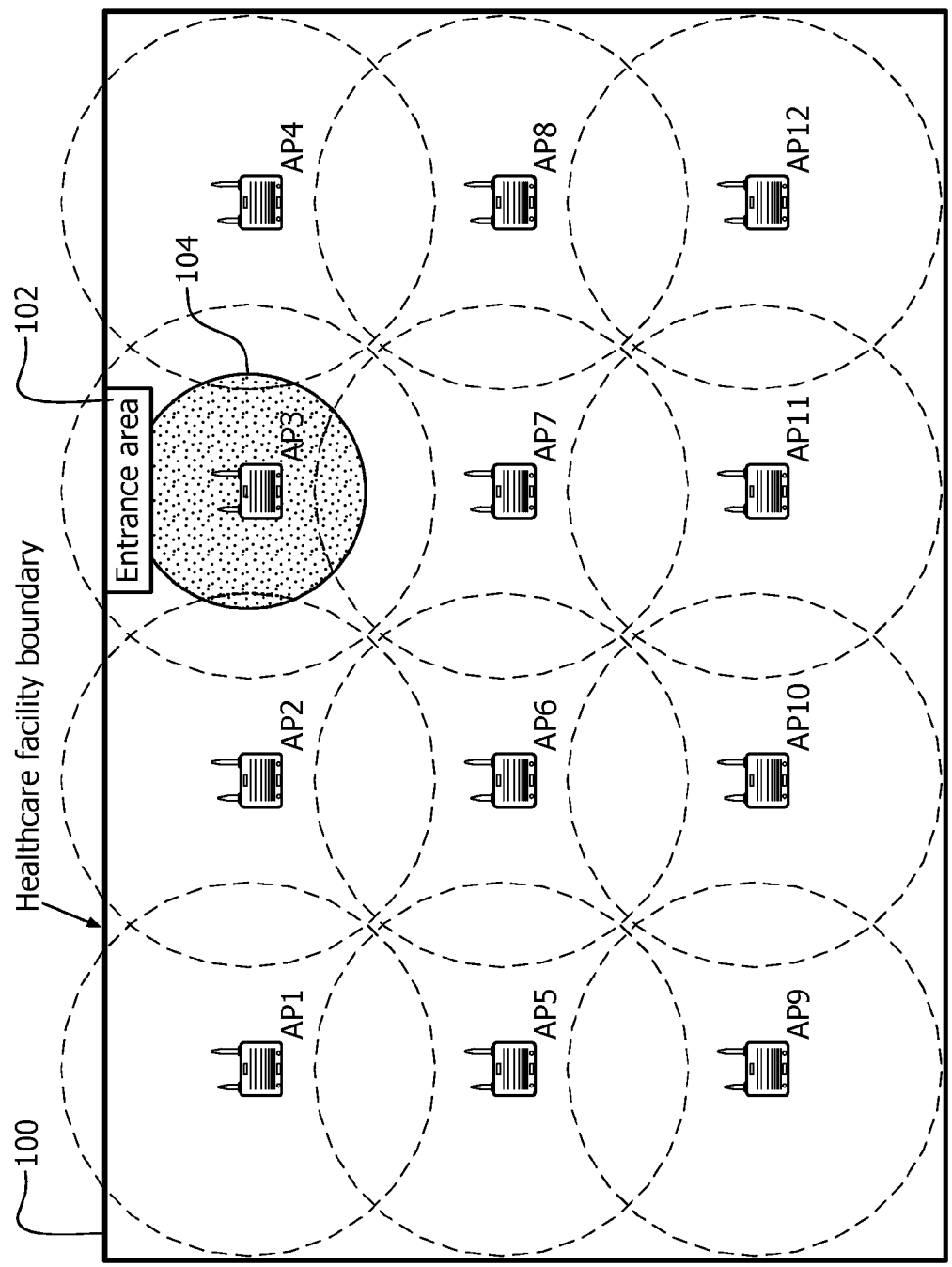

FIGS. 2 and 3 diagrammatically illustrate examples of access point deployments in a healthcare facility in accordance with the present application.

Figure 4:
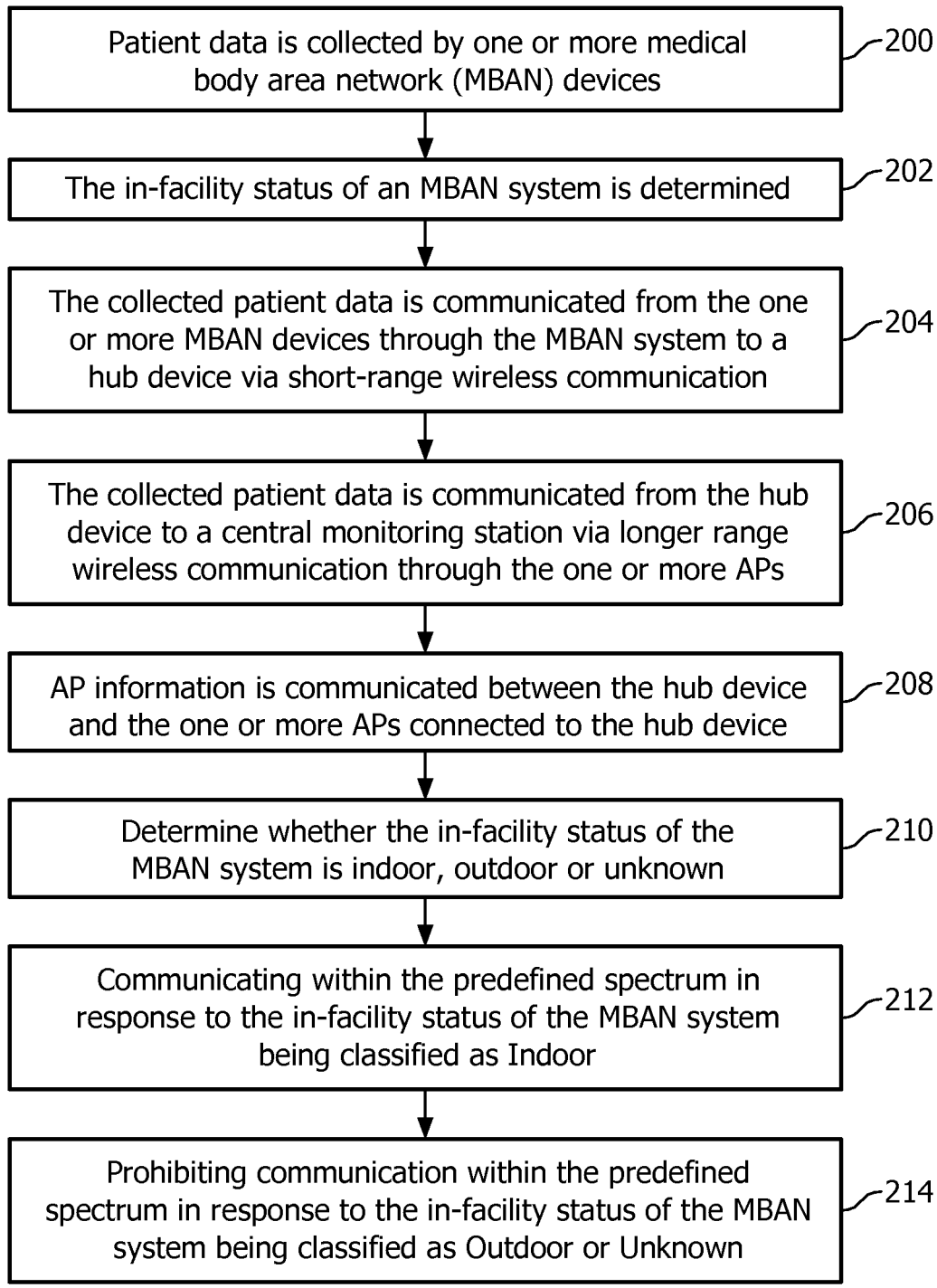

FIG. 4 is a flowchart diagram of the operation of the MBAN system in accordance with the present application.

With reference to FIG. 1, each medical body area network (MBAN) 10 of a plurality of MBANs includes a plurality of MBAN devices 12, 14 and a corresponding hub device 16. The MBAN devices 12, 14 communicate with the corresponding hub device 16 via a short-range wireless communication protocol. The MBAN 10 is also sometimes referred to in the relevant literature by other equivalent terms, such as a body area network (BAN), a body sensor network (BSN), a personal area network (PAN), a mobile ad hoc network (MANET), or so forth—the term medical body area network (MBAN) 10 is to be understood as encompassing these various alternative terms.

The illustrative MBANs 10 includes two illustrative MBAN devices 12, 14 and a corresponding hub devices 16; however, the number of MBAN devices and hub devices can be one, two, three, four, five, six, or more, and moreover the number of MBAN devices may in some embodiments increase or decrease in an ad hoc fashion as MBAN devices are added or removed from the network to add or remove medical monitoring capability. The MBAN devices 12, 14 include one or more sensors 20 that acquire patient data including physiological parameters such as heart rate, respiration rate, electrocardiographic (ECG) data, or so forth; however, it is also contemplated for one or more of the MBAN devices to perform other functions such as controlled delivery of a therapeutic drug via a skin patch or intravenous connection, performing cardiac pacemaking functionality, or so forth. Other MBAN devices can be associated with a patient, and not all of the above-mentioned MBAN devices have to be associated with a patient at any given time. A single MBAN device may perform one or more functions. The illustrative MBAN devices 12, 14 are disposed on the exterior of an associated patient; however, more generally the MBAN devices may be disposed on the patient, or in the patient (for example, a MBAN device may take the form of an implanted device), or proximate to the patient within the communication range of the short-range communication protocol (for example, a MBAN device may take the form of a device mounted on an intravenous infusion pump (not shown) mounted on a pole that is kept near the patient, and in this case the monitored patient data may include information such as the intravenous fluid flow rate). It is sometimes desirable for the MBAN devices to be made as small as practicable to promote patient comfort, and to be of low complexity to enhance reliability—accordingly, such MBAN devices 12, 14 are typically low-power devices (to keep the battery or other electrical power supply small) and may have limited on-board data storage or data buffering. As a consequence, the MBAN devices 12, 14 should be in continuous or nearly continuous short-range wireless communication with the corresponding hub device 16 in order to expeditiously convey acquired patient data to the corresponding hub device 16 without overflowing its data buffer.

In FIG. 1, the short-range wireless communication range is diagrammatically indicated by the dotted line used to delineate the MBAN system 10. The short-range wireless communication is typically two-way, so that the MBAN devices 12, 14 can communicate information (e.g., patient data, MBAN device status, or so forth) to the corresponding hub device 16; and the corresponding hub device 16 can communicate information (e.g., commands, control data in the case of a therapeutic MBAN device, or so forth) to the MBAN devices 12, 14. The illustrative hub device is a waist-mounted device which facilitates carrying a longer, heavier battery and other hardware for longer range transmissions; however, the hub device can be otherwise mounted to the patient, for example as a wrist device, adhesively glued device, or so forth. It is also contemplated for the hub device to be mounted elsewhere proximate to the patent, such as being integrated with an intravenous infusion pump (not shown) mounted on a pole that is kept near the patient.

The patient data acquired from the sensors 20 is concurrently transmitted to a controller 22 in the corresponding MBAN device. The MBAN devices 12, 14 serve as a gathering point for the patient data acquired by the sensors 20 and provide temporary storage of the patient data in a memory 24.

The MBAN devices 12, 14 also include a communication unit 26 for transmitting the patient data via short-range wireless communication protocol to the corresponding hub device 16. The communication unit 26 include a transceiver (not shown) to transmit the patient data and information, received by the controller 22, and receive information, from the hub device 16.

The short-range wireless communication protocol preferably has a relatively short operational range of a few tens of meters, a few meters, or less, and in some embodiments suitably employs an IEEE 802.15.4 (Zigbee) short-range wireless communication protocol or a variant thereof, or a Bluetooth™ short-range wireless communication protocol or a variant thereof. Although Bluetooth™ and Zigbee are suitable embodiments for the short-range wireless communication, other short-range communication protocols, including proprietary communication protocols, are also contemplated. The short-range communication protocol should have a sufficient range for the hub device 16 to communicate reliably with all MBAN devices 12, 14 of the MBAN system 10. The short-range wireless communication protocol between the MBAN devices 12, 14 and the corresponding hub device 16 and in some embodiments between MBAN devices operate in a frequency spectrum of around 2.3-2.5 GHz.

Due to the strict reliability requirements on MBAN system 10 communications because of the medical content of the patient data being transmitted, an MBAN spectrum is specifically allocated for the communication of the patient data, for example, the 2360-2400 MHz band discussed above. The reliability requirements make the MBAN spectrum preferable for patient data transmission to other available spectrum. Once an MBAN hub device is located within the healthcare facility, it will be able to setup and operate an MBAN network within part or the entire of the MBAN spectrum. As long as the MBAN devices 12, 14 are associated with the MBAN hub 16 in the MBAN network, they can communicate with the MBAN hub 16 over the MBAN spectrum.

In the MBAN spectrum, the MBAN devices 12, 14 are secondary users of the spectrum. In order to protect primary users, operation of MBAN devices 12, 14 in the MBAN spectrum is prohibited unless the MBAN devices 12, 14 are authorized to operate in the MBAN network. Specifically, MBAN operations in the MBAN spectrum are limited to healthcare facilities only, meaning the MBAN devices 12, 14 are only allowed to transmit in the MBAN spectrum only when they are located within a healthcare facility. When the MBAN devices are outside the healthcare facility, the MBAN devices are required switch to a new channel outside the MBAN spectrum to transmit data. For example, the MBAN devices are only allowed to transmit patient data over the MBAN spectrum when the MBAN device is within the healthcare facility.

The hub device 16 coordinates operation of its MBAN system 10 over the MBAN spectrum to receive the patient data acquired by the sensors 20 of the MBAN devices 12, 14 and transmit the collected patient data from the MBAN 10 via a longer range communication protocol to a central monitoring station 34. The patient data acquired from the sensors 20 is concurrently transmitted from the MBAN devices 12, 14 to a short range communication device 28 in the corresponding hub device 16. The hub device 16 serves as a gathering point for the patient data acquired by the sensors 20 of all the MBAN device 12, 14 in the MBAN network, e.g. all of the MBAN devices associated with one patient, and provides temporary storage of the patient data in a memory 30. The hub device 16 also includes a longer communication unit 32 for transmitting the patient data via a longer range wireless communication protocol to the central monitoring station 34. A controller 33 of the MBAN hub 16 controls communication with the MBAN devices 12, 14, collection and handling of the patient data, retransmission of the patient data to the central monitoring station 34, setting up the network, associating new MBAN devices, disassociating removed MBAN devices, and the like.

The longer communication unit 32 of the hub device 16 also includes a transceiver which provides the longer-range communication capability to communicate data off the MBAN system 10. In the illustrative example of FIG. 1, the hub device 16 wirelessly communicates with a central monitoring station 34 through an access point (AP) 36 of a hospital network 42. The illustrative AP 36 is a wireless access point that communicates wirelessly with the hub device 16. In the illustrative embodiment the hospital network 42 also includes additional access points, such as illustrative access points AP 38 and AP 40 that are distributed throughout the hospital or other medical facility. To provide further illustration, a central monitoring station is diagrammatically indicated, which is in wireless communication with the AP 24. Different APs 36, 36, 40 cover different areas of the healthcare facility and their coverage areas could overlap with each other to provide seamlessly roaming service. The positions of APs are fixed and known and can be used to determine the location of the MBAN hub device 16, particularly whether the patient is located within or outside the healthcare facility. Location can be determined in various ways, such as a GPS in the MBAN hub, triangulation between the closest APs, calculating and projecting a trajectory from previously contacted APs, and the like. Specifically, when a particular hub device is communicating with an AP, information about the AP is communicated to the MBAN hub device 16. The information includes the identification of the AP, classification of the AP, location of the AP, the identification of the hospital network of which the AP is connected, and the like. The MBAN hub device 16 utilizes this information to determine whether it is authorized to operate in the MBAN spectrum.

To provide further illustration, the central monitoring station 34 includes a controller 44 for receiving the patient data from many hub devices. The central monitoring station 34 also includes a display monitor 46 that may, for example, be used to display medical data for the patient that are acquired by the MBAN system 10 and communicated to the central monitoring station 34 via the AP 38 of the hospital network 42. The central monitoring station 34 also communicates with an electronic patient records sub-system 48 in which patient data and records for all current and past patients is stored. Communication between the central monitoring stations and the electronic patient records sub-system 48 is communicated via AP 40 of the hospital network 42. The longer-range wireless communication is suitably a WiFi communication link conforming with an IEEE 802.11 wireless communication protocol or a variant thereof. However, other wireless communication protocols can be used for the longer-range communication, such as another type of wireless medical telemetry system (WMTS). Moreover, the longer range communication can be a wired communication such as a wired Ethernet link (in which case the hospital networks include at least one cable providing the wired longer range communication link).

The longer range communication is longer range as compared with the short-range communication between the MBAN devices 12, 14 and the corresponding hub device 16. For example, the short-range communication range may be of order ameter, a few meters, or at most perhaps a few tens of meters. The longer range communication can be long enough to encompass a substantial portion or all of the hospital or other medical facility whether directly or via a plurality of AP to a hospital network.

The longer-range communication, if wireless, requires more power than the short-range communication—accordingly, the hub device 16 includes a battery or other power source sufficient to operate the longer-range communication transceiver. The hub device 16 also typically includes sufficient on-board storage so that it can buffer a substantial amount of patient data in the event that communication with the hospital network 34 is interrupted for some time interval. In the illustrative case of wireless longer-range communication, it is also to be understood that if the patient moves within the hospital or healthcare facility then the IEEE 802.11 or other wireless communication protocol employed by the hospital network 34 provides for the wireless communication. In this regard, although the patient is typically as lying in a bed, more generally it is contemplated for the patient to be ambulatory and to variously move throughout the hospital or healthcare facility. As the patient moves, the MBAN system 10 including the MBAN devices 12, 14 and the hub device 16 move together with the patient.

In the MBAN 10, the MBAN devices 12, 14 communicate with the hub device 16 via the short-range wireless communication. However, it is also contemplated for various pairs or groups of the MBAN devices 12, 14 to also intercommunicate directly (that is, without using the hub devices 16, 18 as an intermediary) via the short-range wireless communication. This may be useful, for example, to coordinate the activities of two or more MBAN devices in time. Moreover, the hub devices 16, 18 may provide additional functionality—for example, the hub devices 16, 18 may also be a MBAN device that includes one or more sensors for measuring physiological parameters. Still further, while the single hub devices 16, 18 is illustrated, it is contemplated for the coordinating functionality (e.g. data collection from the MBAN devices 12, 14 and offloading of the collected data via the longer range wireless communication) to be embodied by two or more MBAN devices that cooperatively perform the coordinating tasks.

In illustrative FIG. 1, only one MBAN system 10 is illustrated in detail. However, it will be appreciated that more generally the hospital or other medical facility includes a plurality of patients, each having his or her own MBAN system. More generally, the number of MBAN systems may be, by way of some illustrative examples: the hundreds, thousands, tens of thousands, or more depending on the size of the medical facility. Indeed, it is even contemplated for a single patient to have two or more different, independently or cooperatively operating MBAN systems (not illustrated). In this environment, various MBAN systems of different patients can be expected to come into close proximity with one another, such that the ranges of the respective MBAN system short-range wireless communications overlap.

The MBAN devices 12, 14, MBAN hub 16, MBAN system 10, and central monitoring station 34 include at least one processor, for example a microprocessor or other software controlled device configured to execute MBAN software for performing the operations described in further detail below. Typically, the MBAN software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

As stated above, MBAN hub device 16 include transceivers that associate with the APs 36, 38, 40 to provide connection to hospital network 42. The positions and coverage areas of the APs are fixed and known. When a MBAN hub device 16 is associated with an AP 36, 38, 40, information about the AP 36, 38, 40 is communicated to the MBAN hub device to determine the location of the MBAN hub device 16. Specifically, the MBAN hub device 16 uses the AP information to determine if the MBAN hub device's 16 current location is in-facility, out-facility, or unknown, and make a decision whether it is allowed to operate in the MBAN spectrum.

As shown in FIG. 2, the APs are classified into three different AP types including inner APs, exterior APs, and entrance APs respectively. To determine the classification of the AP, the healthcare facility includes a healthcare facility border 100 and a healthcare entrance area 102. If an AP coverage includes the entrance area 102, e.g. front door lobby, back door, other exits, balcony, and the like, the AP is classified as an entrance AP. For example, AP3 is an entrance AP because it covers an entrance area of the healthcare facility. If an AP has a coverage area that extends outside healthcare facility boundary 100 (or in other words, if an MBAN hub device can successfully connect to an AP even if the MBAN hub is outside healthcare facility), then the AP is classified as an exterior AP. For example, AP1, AP2, and AP4 are exterior APs since part of their coverage areas are outside healthcare facility. If the coverage area of an AP is completely within healthcare facility (or in other words, an MBAN hub device cannot successfully connect to the AP if the hub device is outside healthcare facility), the AP is classified as inner AP. For example, AP5-AP12 in FIG. 2 are classified as inner APs. When a MBAN hub device is associated with an AP, the classification of the AP is communicated and stored as a parameter in the MBAN hub device and used to determine if the MBAN hub device is within or outside the healthcare facility.

The MBAN hub devices include in-facility status parameters to indicate their location or status. The in-facility status parameters include three values: Indoor, Outdoor, and Unknown. When the MBAN hub connects to an AP, the in-facility status parameter of the MBAN hub device will be set based on the classification of the AP the hub connects to. For example, when an MBAN hub device starts to operate, the parameter is set to the default value "Unknown" or manually set by healthcare staff. If an MBAN hub device connects to an Entrance AP, the MBAN hub device parameter will be set to "Outdoor". If an MBAN hub device connects to an inner AP, the MBAN hub device parameter will be set to "Indoor". If an MBAN connects to an exterior AP, the MBAN hub device parameter will keep unchanged. If an MBAN hub loses its connection to the AP, the MBAN hub device parameter will be reset to the default value "Unknown". The MBAN hub device continuously or periodically checks the classification of the AP to which it is connected and updates its in-facility status parameter accordingly. The above proposed scheme only uses AP information to determine the in-facility status of an MBAN hub device and does not require any extra hardware components.

If the in-facility status parameter of an MBAN hub device is "Indoor", the MBAN hub device and its associated MBAN devices are treated as if they are located within healthcare facility and are allowed to communicate within the MBAN spectrum. When the parameter of an MBAN hub device is "Outdoor" or "Unknown", the MBAN hub device and its MBAN devices are treated as if they are located outside healthcare facility and are not allowed to operate in the MBAN spectrum. If an MBAN hub device is operating within the MBAN spectrum and the parameter of the MBAN hub device is changed to "Outdoor" or "Unknown", the MBAN hub device will stop transmissions within MBAN spectrum.

The MBAN hub device also includes an AP signal strength indicator (SSI) measured at the MBAN hub device or AP. The SSI indicates the strength of signal from the connected AP. The SSI and the AP classification are used by the MBAN hub device to determine the in-facility status of an MBAN. As stated above, when an MBAN hub device starts to operate, the in-facility status parameter is set the default value "Unknown" or manually set by healthcare staff. If an MBAN hub device connects to an Entrance AP and the SSI is less than a predetermined entrance boundary signal strength, the MBAN hub device parameter is set to "Outdoor". When a MBAN hub device connects to an Entrance AP, the in-facility status parameter of the MBAN hub device will be set to "Indoor" if the SSI is greater than or equal to the predetermined entrance boundary signal strength. If an MBAN hub device connects to an inner AP, the MBAN hub device parameter is set to "Indoor". If an MBAN hub device connects to an exterior AP and the SSI is less than a predetermined exterior boundary signal strength, the MBAN hub device parameter keeps unchanged. When the MBAN hub device connects to an exterior AP, the MBAN hub device in-facility status parameter is set to "Indoor", if the SSI is greater than or equal to the predetermined exterior boundary signal strength. If an MBAN hub loses its connection to APs, then it will reset the parameter to the default value "Unknown". The SSI related criteria could be implemented either at MBAN hub device side or at AP side. Each of the exterior and entrance APs may have its own predetermined boundary signal strength parameters to optimize performance. The enhanced criteria would allow more in-facility areas to possibly use the MBAN spectrum and therefore improve spectrum usage efficiency. For example, in FIG. 3, if an MBAN is connecting with AP3 and in the circle 104, which is the region that has SSI is greater than or equal to the predetermined entrance boundary signal strength, the MBAN hub device will be treated as "Indoor" and allowed to operate in the MBAN spectrum.

Once the MBAN has left the hospital network area and started communicating on the non-MBAN spectrum, it can be re-authorized to use the MBAN spectrum using any of various network formation techniques. For example, the hospital network can use the communications on the non-MBAN spectrum to establish "Indoor" location criteria. As another example, the MBAN hub device can listen for beacon signals on the MBAN spectrum to tell if it is within range and to go through a re-introduction protocol.

To further improve the MBAN spectrum efficiency, neighbor AP information is utilized to determine MBAN in-facility status. For example, the MBAN hub device utilized both the connected AP information and neighboring AP information to track the movement of the MBAN hub device and determine the location of the MBAN hub device. When an MBAN device starts to operate; the parameter is set to the default value "Unknown" or manually set by healthcare staff. If an MBAN connects to an Indoor AP, then its parameter is set to "Indoor". If an MBAN connects to an Entrance AP, then its parameter is set to "Indoor", if the SSI is greater than or equal to the predetermined entrance boundary signal strength. If an MBAN connects to an Entrance AP and finds a neighbor AP classified as an indoor AP, and the SSI from the neighbor AP is greater than or equal to the predetermined neighbor boundary signal strength, the MBAN hub device parameter is set to "Indoor". Otherwise the MBAN hub device parameter is set to "Outdoor" when an MBAN connects to an Entrance AP. If an MBAN connects to an Exterior AP, then its parameter is set to "Indoor", if the SSI is greater than or equal to the predetermined exterior boundary signal strength. If the MBAN hub parameter's current value is "Outdoor" and the SSI is less than the predetermined exterior boundary signal strength but the MBAN hub device finds at least one neighbor "Indoor" AP and the SSI from the neighbor AP is greater than or equal to the predetermined neighbor boundary signal strength, the MBAN hub parameter is set to "Indoor" when the MBAN hub device connects to an Exterior AP. If the parameter's current value is "Outdoor" and the SSI is less than the predetermined exterior boundary signal strength and the MBAN hub does NOT find any neighbor "Indoor" AP from which the SSI is greater than or equal to the predetermined neighbor boundary signal strength, the MBAN hub parameter will remain "Outdoor" when the MBAN connects to an Exterior AP. If the MBAN hub device parameter's current value is "Unknown" and the MBAN hub find a neighbor "Indoor" AP and the SSI from that neighbor AP is greater than or equal to the predetermined neighbor boundary signal strength, the MBAN hub device parameter will be set to "Indoor" if an MBAN connects to an Exterior AP. Otherwise the MBAN hub device parameter keeps unchanged if an MBAN connects to an Exterior AP. More sophisticated solutions could be possible by using the observed neighbor APs and their SSI information, the associated AP and its SSI to characterize entrance areas and/or inner areas. In such case, the criteria can be specifically designed for individual AP.

FIG. 4 illustrates the operation of the MBAN system. In a step 200, patient data is collected by one or more medical body area network (MBAN) devices. In a step 202, the in-facility status of an MBAN system is determined. In a step 204, the collected patient data is communicated from the one or more MBAN devices through the MBAN system to a hub device via short-range wireless communication, the communication via short-range wireless communication within a predefined spectrum is permitted only within a healthcare facility. In a step 206, the collected patient data is communicated from the hub device to a central monitoring station via longer range wireless communication through the one or more APs. In a step 208, AP information is communicated between the hub device and the one or more APs connected to the hub device. In a step 210, it is determined whether the in-facility status of the MBAN system is indoor, outdoor or unknown based on AP information. In a step 212, the predefined spectrum is communicated in response to the in-facility status of the MBAN system being classified as Indoor. In a step 214, communication is prohibited within the predefined spectrum in response to the in-facility status of the MBAN system being classified as Outdoor or Unknown.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A medical system comprising:
   one or more medical body area network (MBAN) devices which acquire and communicate patient data;
   one or more MBAN systems, each MBAN system including:

the one or more MBAN devices communicating the patient data with a hub device via short-range wireless communication, the communication of the patient data via the short-range wireless communication being within a predefined spectrum;

the hub device which receives patient data communicated from the one or more MBAN devices, communicates with a central monitoring station via a longer range communication and one or more access points (AP), and determines the location of the MBAN system in reference to a healthcare facility;

wherein signal strength of the AP is used to determine in-facility status of the MBAN system;

wherein the one or more MEAN devices are inhibited from transmitting within the predefined spectrum when the MBAN hub device is located outside the healthcare facility; and wherein:
in response to the hub device being connected to an Entrance AP, the in-facility status is either set to Indoor if the AP signal strength is greater than or equal to a predefined threshold or set to Outdoor if the AP signal strength is less than the predefined threshold; and
in response to the hub device being connected to an Exterior AP, the in-facility status is either set to Indoor if the AP signal strength is greater than or equal to a predefined threshold or keeps unchanged if the AP signal strength is less than the predefined threshold.

2. A method comprising:

collecting patient data by one or more medical body area network (MBAN) devices;

determining whether an MBAN system is entering or leaving a healthcare facility from one or more Entrance Access Points (APs) of a healthcare facility network, including determining whether a hub device is connected to one of the one or more Entrance APs;

in response to the hub device connecting to one of the one or more Entrance APs and the AP signal strength exceeding a threshold determining that the hub device has entered into the healthcare facility and communicating the collected patient data from the one or more MBAN devices to the hub device via short-range wireless communication within a predetermined spectrum; and in response to the hub device connecting to one of the one or more entrance devices and the AP signal strength being less than the threshold, determining that the hub device is exterior to the healthcare facility and inhibiting the MBAN device and the hub device from communicating with each other within the predefined spectrum and communicating the collected patient data from the hub device to the central monitoring station via longer range wireless communication through the one or more Entrance APs.

3. A medical system comprising:

one or more processors programmed to perform the method according to claim 2.

4. A non-transitory computer readable medium containing software which when loaded into a processor programs the processor to perform the method according to claim 2.

* * * * *